United States Patent
Pison et al.

(10) Patent No.: US 9,247,928 B2
(45) Date of Patent: Feb. 2, 2016

(54) BIOPSY INSTRUMENT COMPRISING A MAGNETIC ELEMENT

(75) Inventors: Ulrich Pison, Berlin (DE); Silvia Pietschmann, Berlin (DE); Wolfgang Meissner, Berlin (DE)

(73) Assignee: OGENO GMBH, Berlin (DE)

( * ) Notice: Subject to any disclaimer, the term of this patent is extended or adjusted under 35 U.S.C. 154(b) by 0 days.

(21) Appl. No.: 13/503,002

(22) PCT Filed: Oct. 20, 2010

(86) PCT No.: PCT/DE2010/001239
§ 371 (c)(1),
(2), (4) Date: Aug. 7, 2012

(87) PCT Pub. No.: WO2011/047671
PCT Pub. Date: Apr. 28, 2011

(65) Prior Publication Data
US 2012/0302916 A1    Nov. 29, 2012

(30) Foreign Application Priority Data

Oct. 20, 2009  (DE) .................. 10 2009 050 361
Jun. 4, 2010   (DE) .................. 10 2010 017 236

(51) Int. Cl.
| | |
|---|---|
| *A61B 5/00* | (2006.01) |
| *A61B 10/02* | (2006.01) |
| *G01N 33/543* | (2006.01) |
| *G01N 33/569* | (2006.01) |
| *A61B 10/04* | (2006.01) |
| *A61B 17/00* | (2006.01) |

(52) U.S. Cl.
CPC .......... *A61B 10/02* (2013.01); *G01N 33/54326* (2013.01); *G01N 33/54346* (2013.01); *G01N 33/569* (2013.01); *A61B 10/04* (2013.01); *A61B 2017/00876* (2013.01)

(58) Field of Classification Search
CPC . A61B 10/007; A61B 10/0045; A61B 5/1405
USPC .................................................. 600/562, 573
See application file for complete search history.

(56) References Cited

U.S. PATENT DOCUMENTS

| | | | | |
|---|---|---|---|---|
| 3,118,439 | A * | 1/1964 | Perrenoud | 600/582 |
| 3,924,607 | A * | 12/1975 | Bucalo | 600/575 |
| 7,309,316 | B1 | 12/2007 | Flynn et al. | |
| 2004/0210289 | A1* | 10/2004 | Wang et al. | 607/116 |
| 2004/0254419 | A1* | 12/2004 | Wang et al. | 600/8 |
| 2005/0025797 | A1* | 2/2005 | Wang et al. | 424/422 |
| 2005/0079132 | A1* | 4/2005 | Wang et al. | 424/1.11 |
| 2005/0107870 | A1* | 5/2005 | Wang et al. | 623/1.44 |
| 2006/0041182 | A1* | 2/2006 | Forbes et al. | 600/12 |
| 2006/0241691 | A1* | 10/2006 | Wilk | 606/215 |
| 2007/0010702 | A1* | 1/2007 | Wang et al. | 600/8 |

(Continued)

FOREIGN PATENT DOCUMENTS

| | | |
|---|---|---|
| WO | 2006/131400 A1 | 12/2006 |
| WO | 2008/110392 A2 | 9/2008 |
| WO | 2010/025719 A1 | 3/2010 |

*Primary Examiner* — Sean Dougherty
*Assistant Examiner* — Daniel Cerioni
(74) *Attorney, Agent, or Firm* — Joyce von Natzmer; Agris & von Natzmer LLP

(57) ABSTRACT

The invention relates to a magnetic biopsy-instrument and use thereof for enriching specific sample material from the body. The invention also relates to a biopsy-kit and use thereof for enriching specific sample material.

28 Claims, 8 Drawing Sheets

(56) References Cited

U.S. PATENT DOCUMENTS

Figure 1:
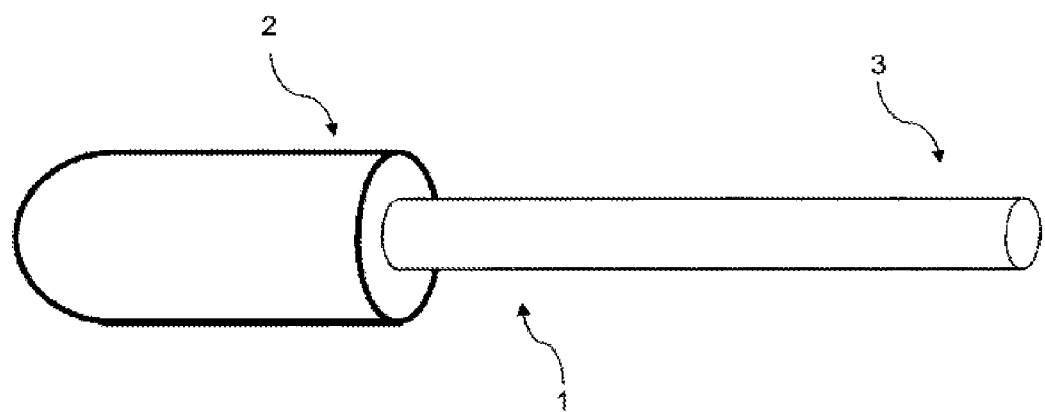

| | | | |
|---|---|---|---|
| 2007/0249999 A1* | 10/2007 | Sklar et al. | 604/101.05 |
| 2008/0213130 A1* | 9/2008 | Pison et al. | 422/68.1 |
| 2009/0131274 A1* | 5/2009 | Pison et al. | 506/12 |
| 2009/0163564 A1* | 6/2009 | Borden et al. | 514/383 |
| 2009/0220418 A1* | 9/2009 | Pison et al. | 424/1.65 |
| 2009/0311190 A1* | 12/2009 | Gracias et al. | 424/9.3 |
| 2010/0004558 A1* | 1/2010 | Frankhouser et al. | 600/567 |
| 2010/0132161 A1* | 6/2010 | Vu | 16/404 |
| 2010/0168609 A1* | 7/2010 | Pison et al. | 600/562 |
| 2011/0213270 A1 | 9/2011 | Pison | |

* cited by examiner 2  8  3

BIOPSY INSTRUMENT COMPRISING A MAGNETIC ELEMENT

CROSS-REFERENCE TO RELATED APPLICATIONS

This is the U.S. national stage of International application PCT/DE2010/001239, filed Oct. 20, 2010 designating the United States and claiming priority to German application no. DE 10 2009 050 361.7, filed Oct. 20, 2009 and German application no. DE 10 2010 017 236.7, filed Jun. 4, 2010.

The present invention relates to a biopsy instrument for the enrichment of specific sample material, wherein the biopsy instrument has a magnetic element. Moreover, the invention relates to a method for binding micro-organisms and to the use of the biopsy instrument for diagnosis, and to a biopsy-kit for the enrichment of cell or molecule samples in different body cavity systems such as, for example, a blood vessel, spinal canal, bile duct, efferent urinary tracts of humans or animals.

In daily clinical practice, bacterial infections cause numerous problems with regard to diagnosis and specific therapies. The Deutsche Sepsis Gesellschaft e.V. has comprehensively presented the clinical importance of sepsis on their website. According to this, the position on pathophysiology of this clinical picture has changed such that no longer the infection caused by the pathogens is the central focus, but the patient's systemic immune response that can be induced through different stimuli. This new perception is in particular influenced by the daily clinical routine where microbiological diagnostics does not provide significant aid to decision-making for the therapy. Identification and sanitation of the site of the sepsis and the rapid antibiotic therapy are given highest priority.

The mortality rate of 40% from sepsis is as high as ever. In the USA, approximately 263,000 people die every year from sepsis and thus more than from acute myocardial infarction. Per 100,000 inhabitants, approximately 300 people suffer from severe sepsis. In comparison to that, there are 17 new cases of AIDS, 50 of colon cancer and 110 of breast cancer per 100,000 inhabitants. The incidence of sepsis has quintupled in the past 20 years in the USA. Patients with sepsis have to be treated on average for 16 days in intensive care units and 32 days in a hospital. In most of the European countries, the epidemiological values for the incidence of sepsis are lower than in the USA. For Germany and Austria, 54-116 cases per year and 100,000 inhabitants are reported. The direct proportional costs (medication, routine laboratory, microbiology, disposables, accommodation, personnel) that incur alone for intensive care treatment of patients with severe sepsis lie at approximately 1.77 billion Euros. Thus, approximately 30% of the budget for intensive care is invested in the treatment of severe sepsis. The indirect costs incurred due to productivity loss are estimated to be approximately another 4.5 billion Euros so that total costs in the amount of approximately 6.3 billion Euros are to be assumed which are caused by severe sepsis in Germany.

The microbiological standard methods for the diagnosis of bacterial pathogens have not substantially changed since 1881 when Pasteur and Sternberg for the first time detected pneumococci from sputum, and Christian Gram established his staining method, which is used today as a standard.

The detection of pathogens if sepsis is suspected is performed on blood cultures. However, the detection of germs in these critically ill patients is often not successful and the antibiotic therapy is normally initiated in the clinic without knowing the resistance pattern. Through early detection of pathogens in these patients, the antibiotic therapy could be carried out more targeted, mortality and morbidity could be improved and therapy costs could be reduced.

Identification and separation of individual cell populations from the blood in vitro is achieved today with functionalized magnetic nanoparticles. The magnetic susceptibility of the particles plays an important role here because this behavior substantially determines the magnetophoretic property of the particles used. The decoration of *E. coli* could be successfully implemented in vitro with magnetic nanoparticles, and magnetotactic bacteria can be displayed in vivo with imaging methods.

Taking material from a living human or animal body for microbiological diagnostic methods is usually performed by obtaining a solid tissue sample through a biopsy or by collecting body fluids, e.g. in the form of a vascular puncture for obtaining a blood sample, or through pleural puncture for obtaining a pleural effusion, or through joint puncture for obtaining synovial fluid, or through spinal canal puncture for obtaining liquor, or in general through the puncture of a body cavity system for obtaining material in liquid or liquid-like form. Furthermore, for microbiological diagnostic, swabs from body regions are taken. Up to now, the prior art describes biopsy instruments which, apart from the conventional punching, cutting and suction methods, use antigen-antibody and ligand-receptor interactions in order to obtain or enrich the biopsy material.

In modern medicine, the biopsy, i.e., removing material from a living human or animal body for the purpose of an examination, is routinely performed by means of different methods such as, for example, microscopy. Typically, such a method is used for the diagnosis of malignant and premalignant cell transformations that indicate the presence of cancerous or precancerous tumors. Routine techniques known as core biopsies during which whole tissue segments are removed for histological examination make use of different types of hollow, needle-shaped biopsy instruments. These instruments have cannulas with a sharp frontal edge or a notched stylet in order to cut into the tissue upon insertion into the selected body region. The tissue piece to be removed as a biopsy sample is received in the cylindrical bore of the cannula. When retracting the biopsy instrument from the body, the sample is retained by means of mechanical means or suction means in the cylindrical bore and is separated during the retracting process from the main body of the tissue. The removed samples typically have a generally elongated cylindrical shape or a longitudinal, semi-cylindrical shape. The quality, e.g. the width, the length and the proportion of crushed cells of biopsy samples for cytological or histological examination is an important factor that influences the examination result. Tissue biopsy samples should reflect the structure of the living tissue as accurate as possible. Accordingly, tension on the samples during excision and removal of tissue as well as during removal from the cannula should be avoided.

Up to know, the prior art describes biopsy instruments which, apart from the conventional punching, cutting and suction methods, use antigen-antibody and ligand-receptor interactions in order to obtain the biopsy material.

U.S. Pat. No. 5,282,476 describes an automated device for the biopsy in which the cannula is attached over a stylet which guides the cannula to the biopsy site. After the insertion, the cannula is driven out beyond the stylet and thereby takes the sample. Suction means are used for retaining the sample. However, because of the suction means, this biopsy instrument has a rather complex structure and requires significant skills in handling. In the hands of an inexperienced user, the instrument can give uncertain results. Furthermore, it is designed for removing material from solid body structures and not from body cavity systems.

Furthermore, instruments or sensor are known which serve for enriching the samples. WO/2006/131400 describes the use of a functionalized surface for the enrichment and recovery of molecules or rare cells, e.g. from fetal trophoblasts in the maternal blood circulation. For this, receptor structures are anchored on the surface of the sensor which react with specific cells or molecules in the bloodstream and thus shall permit the enrichment of this material in situ prior to removal from the body.

Furthermore, in the prior art, devices are described (for example WO01/23031 A1, EP 1 779 816 A2, US 2003/0135153, WO 98/22022 A1) with the aid of which certain active ingredients or dyes can be introduced in body cavities. Here, the active ingredients are introduced in cavities of the devices and released upon reaching the target position. The disadvantage here is that the samples are obtained in a very inexact manner and the active ingredients are to be introduced into the devices in liquid form. Hereby, the possible fields of use are greatly limited.

Moreover, in the prior art, magnetic devices are described which are completely or substantially completely magnetic. However, the devices do not allow an optimal enrichment or removal of the sample.

The means described in the prior art for removal or enrichment of samples cannot be used in all areas of the body. In particular, the endoscopic use of the described instruments/sensors is not possible or can only be performed with difficulty. Other important disadvantages are the accuracy with which the tissue areas, in particular body cavity systems, selected for the biopsy can be targeted with the instrument/sensor, the ease with which the instrument/sensor can be handled, injury caused to the patient by the method, as well as the cost of the instrument or the sensor. In addition, no biopsy instrument is described which is designed for use in humans and animals so as to allow enrichment of the biopsy material in a low-risk manner prior to the removal of the sample.

In the case of applications of biopsy instruments which are intended to obtain biopsy material via antigen-antibody or generally via ligand-receptor interactions and which for the purpose of enrichment are implanted in the body for a defined time, it has been found that a plurality of factors make this enrichment under flow conditions difficult. This includes the affinity of the ligand used to its corresponding receptor, the viscosity of the flow medium (e.g. blood in the circulatory system), the flow conditions (velocity, flow regime), the size of the target object and the spatial distance over which the attractive forces have to ensure an enrichment of analytes.

Based on this prior art, it is an object of the present invention to provide a biopsy instrument which does not have the disadvantages or shortcomings of the prior art and which allows the specific enrichment of sample material also by means of endoscopic means and from body cavity systems, and allows subsequent diagnostic methods during the dwell time in the body. Another object of the invention is the development of a biopsy instrument which minimizes the risk of injury to the patient because, in particular, the dwell time of the biopsy instrument within the body for the diagnostic method is a new criterion for sample extraction.

Surprisingly, this object is achieved by the features of the independent claims. Preferred embodiments of the invention arise from the sub-claims.

It was a complete surprise that a biopsy instrument for enriching sample material can be provided which does not have the disadvantages and shortcomings of the prior art and comprises the following components:

i. a guide element comprising a spring-elastic distal portion and a proximal portion,
ii. a magnetic element that is attached between the distal and the proximal portions of the guide element, and
iii. a stabilizing element connected with the proximal portion of the guide element.

It was surprisingly found that the use of a magnetic element within a biopsy instrument results in that biopsy material can be obtained even under difficult flow conditions. In the case of the magnet biopsy devices disclosed in the prior art, which are either completely magnetic or comprise a plurality of magnetic elements or components, there are strong interactions between the magnetic elements, which makes removing the samples more difficult. In addition, it was found that the magnetic field generated here can have an influence on organs or tissue. Because the biopsy instrument according to the invention comprises only one magnetic element, the magnetic field, on the one hand, is so weak that no interactions with tissues or organs are generated and, on the other, there are no interactions within the biopsy instrument.

The biopsy instrument is used for enriching sample material. This can involve, in particular, a sample from the group comprising blood or blood plasma, chyle or lymph, urine, semen, vaginal secretions, amniotic fluid, saliva, gastric juice, bile, pancreatic juice, nasal secretions, bronchial secretions, alveolar fluid, liquor, endolymph, aqueous humor, tears, synovial fluid, pleural fluid, pericardial fluid (liquor pericardii), peritoneal fluid, breast milk, sweat, menstrual fluid or combinations thereof or other samples from the area of the biopsy.

The biopsy instrument consists of at least one guide element, a magnetic element and a stabilizing element. The guide element has a distal and a proximal portion, wherein the distal portion is spring-elastic. In the meaning of the invention, the terms "proximal" and "distal" refer to the person taking a biopsy sample. Accordingly, the proximal end of the biopsy instrument is in particular the rear end that faces away from the patient.

The term "spring-elastic" in the meaning of the invention describes in particular the property of a material to deform under load and to regain the substantially original shape when released from the load. This property of the distal portion of the guide element advantageously ensures that there is little to no risk of injury to the patient because the spring-elastic portion deforms upon contact with a surface such as, e.g., a vessel wall or an organ, and thus the pressure on the surface is reduced.

Between the distal and the proximal portions of the guide element, a magnetic element is attached. A magnetic element in the meaning of the invention is in particular an element that advantageously has a magnetic field or can generate a magnetic field. Said magnetic element can be made from a magnetic material or can comprise a magnetic alloy. However, it can also be preferred that a magnetic adhesive tape is applied onto the magnetic element. Accordingly, it can be preferred that the magnetic elements include magnetic materials comprising metal, plastic and/or ceramic materials. In the meaning of the invention, these materials comprise in particular materials which, for example, are permanently magnetized under the influence of an external magnetic field. The magnetic materials comprise advantageously ferromagnetic materials in which the magnetization takes place through a potential rapid alignment of the Weiss' domains under the influence of an external magnetic field. Preferred ferromagnetic materials comprise iron or soft iron, silicon iron, permalloy, supermalloy, cobalt, nickel, Mn—Zn ferrites and Alnico V, lanthanides, gadolinium, terbium, dysprosium, holmium and erbium. Preferably, neodymium and/or samarium cobalt are used as a magnetic material. However, it can also be preferred that an electromagnet is used as a magnetic element. Advantageously, the electromagnet can be switched on and off. This allows activating the electromagnet only at the biopsy site. An electromagnet comprises in particular a coil in which a core from a ferromagnetic material is located.

Advantageously, it is also possible to use compounds as a magnetic element which do not show a ferromagnetic behavior, for example chromium dioxide, manganese arsenide, europium(II)oxide, superfluid A-1 phase of He-3 or Heusler alloys. However, paramagnetic materials comprising manganese, palladium and chromium or ferrites with the general composition $MIIFeIII_2O_4$ or $MIIO.Fe_2O_3$, which contain permanent magnetic dipoles, can advantageously also be used as a magnetic element. Preferably, permanent or hard magnets are used as a magnetic element. Advantageous permanent magnets comprise AlNiCo-, SmCo-, $Nd_2Fe_{14}B$-, $Ni_{80}Fe_{20}$-alloys or NIFeCo alloys with the main constituents Fe, Co, Ni, Al, Cu and Ti. Further preferred magnetic elements comprise PtCo-, FeCoVCr- and SECo-alloys. Since permanent magnets are very hard and brittle, biopsy instruments with surprising advantages can be formed. For example, it was found that this allows an optimal guidance of the biopsy instrument through body cavities, and it is not susceptible to flows.

Preferably, the magnetic element can comprise detection molecules on its surface which are applied onto said element's surface by means of chemical, electrochemical and/or biological methods. Detection molecules are in particular also known to the person skilled in the art as capture molecules. These are molecules which preferably interact with organic and inorganic materials. For example, polymers can be used as organic materials. Approximately 90% of the organic materials are composed of, among other things, carbon, hydrogen and oxygen in changing proportions. Organic compounds can also contain nitrogen, sulfur, phosphor and halogens, but also other elements or combinations thereof. Furthermore, metallo-organic materials comprising, among other things, a compound from metal and/or carbon can also be used. As inorganic materials, i.e. materials which do not substantially consist of carbon, materials comprising different types of glass, ceramics, nanostructured and nanocrystalline hard materials, silicon or silicates can be used. Thus, due to the special configuration of the magnetic element, an enrichment of special cells or molecules can take place in the body of humans or animals, i.e. in situ, which represents a movement away from the usual technology and solves a long-standing problem of the prior art. Due to a high specificity of the magnetic element, a fast enrichment of sample material is achieved and the patient is treated gently and relieved from stress.

In the proximal portion of the guide element, the stabilizing element is located, which can be fixedly connected to said portion or can be configured to be freely movable. The stabilizing element fixes the magnetic element during the biopsy thereby preventing dislocation of the magnetic element. Also, through the inventive embodiment of the biopsy instrument, removal of the whole instrument from the body of the patient is guaranteed, i.e., through the arrangement of the components, dislocation of individual components is prevented so that no component of the instrument remains in the body of the patient.

Accordingly, the teaching according to the invention describes a biopsy instrument that allows in a surprisingly simple manner to enrich cell or molecule samples in different body cavity system of humans and animals in order to achieve, unlike the devices of the prior art, an optimal concentration for subsequent diagnostic methods. Tests have shown that antibody-antigen bonds are not very stable so that collected sample material gets lost during the removal or the movement of the biopsy instrument. In addition, the interaction between antigen-antibody is made difficult due to the flow conditions prevailing at the sites where the biopsy instrument is positioned. Thus, it was a total surprise that the biopsy instrument according to the invention does not show these disadvantages since collecting the biological sample material is achieved by means of a magnetic element. Specific cells or molecules to be collected can preferably be marked, e.g., by magnetic nanoparticles and can be captured by the inventive biopsy instrument or the magnetic element. The marked samples can be isolated from a body or system without significant losses.

It was a complete surprise that a biopsy instrument in which only a single particular element is magnetic, shows a previously unknown or superior effect with respect to a completely magnetic biopsy instrument, wherein the instrument has no magnetic guide element and no magnetic stabilizing element. In biopsy instruments which are completely or substantially completely magnetic, there are strong magnetic interactions between individual elements which have a negative effect on the sample enrichment. Also, the magnetic biopsy instruments described in the prior art are very susceptible to faults and voluminous. In addition, the production and maintenance costs of such instruments are very high. It was completely surprising that the biopsy instrument according to the invention does not have these disadvantages. The biopsy instrument can be produced in a cost-effective manner, wherein the magnetic element can be connected to the guide element in a simple manner. After sampling, for example, the element can be transferred for analyzing the sample, and an unused magnetic element is attached on the biopsy instrument in a simple and fast manner. Advantageously, the size of the magnetic element is independent of the size of the biopsy instrument so that also small and flexible biopsy instruments can be produced.

The magnetic element of the biopsy instrument can be made in particular from ferromagnetic materials or from an electromagnetic detector. With both techniques, the same goal is achieved, namely efficient and fast enrichment of specific sample materials, binding microorganisms, and the use as a diagnostic instrument, and also, within a biopsy-kit, enriching cell and molecule samples in different body cavity systems.

Further advantages if the inventive biopsy instrument are the accuracy with which the instrument can be positioned in the body region selected for the enrichment of samples, the specificity and sensitivity with which the cells and molecules can be enriched in situ, and the ease with which the biopsy instrument can be handled. Also, the cost of the biopsy instrument is low. A fast and reliable enrichment of samples for analysis plays an important role in medicine and is a decisive criterion for the diagnosis of diseases.

Preferably, the components of the biopsy instrument are arranged sequentially from distal to proximal. The magnetic element is arranged following the spring-elastic guide element, wherein the stabilizing element is located in the proximal portion of the guide element. This arrangement ensures that when inserting the biopsy instrument into the body, the spring-elastic portion is distally arranged, thereby minimizing the risk of injury to the patient. The magnetic element is advantageously fixed by the proximal stabilizing element. Thus, a dislocation of the components during the sample enrichment is prevented, and a loss of a component of the biopsy instrument is prevented. Moreover, through the sequential arrangement of the components, the reliability is increased and the efficiency of a biopsy is improved. A knowledgeable person skilled in the art is capable to construct special forms of the biopsy instrument in which a magnetic element with different detection molecules is arranged between the distal and proximal portions of the guide element, or the functionalization of the distal portion of the guide element takes place with detection molecules while maintaining the spring-elastic material properties of this region.

Furthermore, it is preferred that the distal portion of the biopsy instrument, thus the spring-elastic portion of the guide element, is made of non-magnetic metallic or non-metallic materials. Accordingly, in a preferred embodiment, it can be made from stainless steel, but also from other metals. Metals refer to chemical elements which, in contrast to the non-metals, are listed in the periodic table to the left of the diagonal dividing line starting with the element beryllium ($2^{nd}$ group) through polonium ($16^{th}$ group), as well as their alloys and intermetallic compounds (comprising Laves phases, Heusler phases, Zintl phases, Hume-Rothery phases, NiTi, Co5, Nb3Sn or Ni3Al) with characteristic metallic properties. Metals comprise aluminum, beryllium, bismuth, lead, chromium, iron, gold, indium, potassium, copper, magnesium, manganese, molybdenum, sodium, nickel, osmium, palladium, platinum, rhodium, ruthenium, silver, tantalum, titanium, vanadium, tungsten, zinc, tin or zirconium. In an advantageous embodiment, an inner wire can be circularly surrounded by an outer wire so that the spring-elastic property is obtained. It should be pointed out that in the meaning of the invention, only the magnetic element consists of a magnetic material.

In a further embodiment, the biopsy instrument, in particular the distal portion of the guide element, can be made from non-metallic materials from which thin cylindrical structures can be formed. Preferred non-metals comprise boron, carbon, phosphor, sulfur, iodine or astatine. A cylinder in the meaning of the invention is in particular an area bordered by two parallel plane surfaces (base and top surfaces) and a lateral surface or cylinder surface which is formed by parallel lines. However, it can also be preferred that the distal portion is angularly shaped.

In a preferred embodiment, polymers can be used for non-metallic materials. In the meaning of the invention, polymers refer in particular to a substance that is composed of a collective of macromolecules (polymer molecules) which are chemically uniformly structured, but usually differ with regard to the degree of polymerization, molecular weight and chain length. In such single-polymer materials, all macromolecules preferably have the same structure and differ only in their chain length (degree of polymerization). Such polymers can be designated as polymer homologues. Polymers can be selected from the group comprising inorganic polymers, organometallic polymers, fully or partially aromatic polymers, homopolymers, copolymers, biopolymers, chemically modified polymers and/or synthetic polymers, and comprise polyethylene, polypropylene, polyvinyl chloride, polystyrene, polyvinyl chloride, polystyrene, polymethylmethacrylate, polyamide, polyester, polycarbonate, polyethylene terephthalate, polyethylene glycol, dendrimers, silicones, proteins, DNA, RNA, carbohydrates or polyhydroxyalkanoates. Preferably, polytetrafluoroethylene is used. The distal portion of the biopsy instrument manufactured from these materials represents a technical progress because through the preferred embodiment, the risk of injury is reduced. The material has spring-elastic properties and thus prevents injury to the surfaces that come into contact with the biopsy instrument.

Furthermore, it is advantageous that the stabilizing element of the biopsy instrument is substantially cylindrically. Due to the advantageous embodiment, the stabilizing element can be fitted in a simple manner onto the proximal portion of the guide element by sliding it onto the proximal portion. Furthermore, the advantageous cylindrical shape achieves an easy insertion and withdrawal of the biopsy instrument and thus increases efficiency.

It is also advantageous that the stabilizing element can be slid over the proximal part of the guide element. The stabilizing element can be fit over the proximal portion of the guide element without the need to remove the other components, in particular the magnetic element. The stabilizing element fixes the magnetic element, which is achieved through an exactly fitting preparation of the component. Exactly fitting in the meaning of the invention means in particular that at least two components are made in such a manner that they are compatible and fit exactly into the position provided for them. The ease with which the stabilizing element can be applied onto the proximal portion of the guide element facilitates the work of the person skilled in the art. Furthermore, after a successful biopsy, the stabilizing element can be easily removed and the enriched samples of the magnetic element can be further processed or transferred to adequate processing stations. Thus, the advantageous embodiment represents serendipity because from a multiplicity of possibilities, one particular possibility has been selected, the result of which could not be predicted and therefore constitutes a patentable serendipity.

Furthermore, it is advantageously provided that the outer diameter of the stabilizing element is preferably equal to the outer diameter of the distal portion of the guide element. In this way, a flat, i.e., planar surface of the biopsy instrument is formed thereby greatly reducing the risk of injury to the patient. Furthermore, through the advantageous embodiment, an easy insertion of the biopsy instrument into regions of the body is guaranteed, and it is ensured that said instrument can be removed again as a whole. As a whole means that the arrangement of the components prevents a dislocation of individual components so that no component of the instrument remains in the body of the patient.

Another advantageous embodiment comprises a biopsy instrument, wherein the stabilizing element is reversibly connected to the proximal portion of the guide element. Preferably, according to this embodiment, the stabilizing element can be removed again from the proximal portion of the guide element after the biopsy in order to release the magnetic element. For carrying out subsequent diagnosis methods, the magnetic element can be sent in the corresponding processing locations, or an analysis of the enriched samples can be performed on site. The advantageous embodiment represents a technical progress because the person skilled in the art can easily assemble the biopsy instrument and can disassemble it again into the individual components after completed sample enrichment. After adequate disinfection, the stabilizing element can thus be used repeatedly, thereby reducing costs.

Furthermore, it is advantageous if the stabilizing element is preferably made of plastic. Plastics refer to materials, the essential constituents of which consist of such macromolecular compounds which are created synthetically or by modifying natural products. In many cases, they are meltable and moldable under certain conditions (heat and pressure). Plastics also include rubbers and chemical fibers. The synthetic raw materials for coatings and the adhesives can be counted among plastics. For the advantageous embodiment, plastics from the group of modified natural substances, synthetic plastics (polycondensates, polymers, polyadducts), thermosetting resins and/or unsaturated polyester resins, comprising cellulose nitrate, cellulose acetate, mixed cellulose esters, cellulose ethers, polyamide, poly carbonate, polyester, polyphenylene oxide, polysulphone, polyvinyl acetal, polyethylene, polypropylene, poly-1-butene, poly-4-methyl-1-pentene, ionomers, polyvinyl chloride, polyvinylidene chloride, polymethyl methacrylate, polyacrylnitrile, polystyrene, polyacetal, fluoroplastics, polyvinyl alcohol, polyvinylacetat, poly-p-xylylene, linear polyurethanes, chlorinated polyether, casein plastics, phenolic resin, urea resin, thiourea resin, melamine resin, epoxy resin, cross-linked polyurethanes, alkyd resin, allyl resin, silicone, polyimide, and/or polybenzimidazole can be used. By using plastics for the configuration of the stabilizing element, biopsy instruments with rubber-elastic properties can be produced which can be placed at different biopsy sites in the body. Through the advantageous embodiment, increased reliability and flexibility can thus be achieved when carrying out a biopsy. Also, the risk of injury to the patient is dramatically reduced because the rubber-elastic embodiment does not injure any surfaces. Furthermore, by using plastics for the configuration, costs can be reduced.

It is advantageously provided that the stabilizing element and the proximal portion of the guide element are mechanically connected, bonded and/or welded. As a result, a stable connection of the proximal portion of the guide element and the stabilizing element is achieved, whereby handling the biopsy instrument is made easier for a person skilled in the art. Through a mechanical connection, the connection can be configured in a reversible manner, for which fasteners known to a person skilled in the art are used. Furthermore, those skilled in the art know of bonds or welds that ensure a secure and permanent connection of the proximal portion and the stabilizing element. The stable connection guarantees that the biopsy instrument can be inserted as a whole into a patient and can also be removed again after the sample enrichment, whereby reliability is improved and the biopsy process itself is simplified.

Furthermore, it is advantageous that the guide element and the stabilizing are made using one manufacturing method, which means that for one application, materials for both components can be used which are adapted in size and shape to the corresponding body regions. An advantageous embodiment is plastic from the group of modified natural substances, synthetic plastics (polycondensates, polymers, polyadducts), thermosetting resins and/or unsaturated polyester resins, comprising cellulose nitrate, cellulose acetate, mixed cellulose esters, cellulose ethers, polyamides, polycarbonates, polyester, polyphenylene oxide, polysulphone, polyvinyl acetal, polyethylene, polypropylene, poly-1-butene, poly-4-methyl-1-pentene, ionomers, polyvinyl chloride, polyvinylidene chloride, polymethyl methacrylate, polyacrylonitrile, polystyrene, polyacetal, fluoroplastics, polyvinyl alcohol, polyvinyl acetate, poly-p-xylylene, linear polyurethanes, chlorinated polyether, casein plastics, phenolic resin, urea resin, thiourea resin, melamine resin, epoxy resin, cross-linked polyurethanes, alkyd resin, allyl resin, silicone, polyimide and/or polybenzimidazole. Through this, it can be achieved that the risk of injury to persons is reduced because a plane surface of the instrument is created. Also, handling the biopsy instrument is made easier for a person skilled in the art, and the production cost of the biopsy instrument can be kept low.

In an advantageous embodiment it is provided that the magnetic element has a substantially cylindrical shape, wherein other geometrical shapes can also be used, comprising polygon, triangle, quadrangle, pentagon, hexagon, heptagon, octagon, nonagon, decagon, ellipse, circle, hyperbola, parabola, superellipse, spherical triangle, cycloide, rosette, helix, sphere, ellipsoid, ellipsoid of rotation, paraboloid, paraboloid of rotation, hyperboloid, oloid or polyeder, or combinations thereof or other shapes. Through the embodiment, the magnetic element can easily be fitted from proximal onto the guide element, wherein after fitting, said magnetic element is spatially fixed by the spring-elastic distal portion and the proximal stabilization element. Hereby, dislocation of the magnetic element can be excluded. Furthermore, the preferred substantially cylindrical shape ensures that the biopsy instrument has a plane surface, and an easy insertion and retraction of the biopsy instrument can be guaranteed. Thus, through the advantageous embodiment, the quality of the sample enrichment can be increased while the time of sample enrichment is reduced.

It was surprisingly found that the size of the magnetic element can be reduced if the element has a rough surface. Through the roughness, the surface of the element can be increased and the dimensions can be decreased. Dimension refers in particular to length and/or width dimensions. This results surprisingly in a more efficient sample enrichment, which is an advantage over the prior art. The use of a magnetic element in a biopsy instrument is therefore a movement away from the usual technology because the prior art describes only instruments which are completely magnetic or substantially completely magnetic. By using a small magnetic element, however, numerous advantages over the prior art can be achieved such as, for example, less non-specific interactions, less susceptible to faults, or no interactions within the biopsy instrument.

Advantageously, the magnetic element has an outer diameter that is greater, equal or smaller, preferably 0.01 to 0.1 mm smaller, than the outer diameter of the distal portion of the guide element. Through the advantageous embodiment it is achieved that the magnetic element can be fitted from proximal onto the guide element, but is spatially limited by the distal portion. The outer diameter of the magnetic element is 0.0001 to 5 mm, preferably 0.001 to 1 mm, particularly preferred 0.01 to 0.1 mm smaller than the outer diameter of the distal region of the guide element. With the preferred outer diameter of the magnetic element, a nearly plane surface of the biopsy instrument can be generated which, surprisingly, guarantees an optimum functionality of the instrument because during insertion and retraction of the biopsy instrument, said instrument does not interact with biological surfaces and therefore, the positioning of the biopsy instrument is not adversely affected. Moreover, it was found that through the preferred outer diameter, particularly efficient sample enrichment can be achieved and the instrument can be sterilized or cleaned in a faster and simpler manner. The outer diameter of the biopsy instrument and accordingly the outer diameter of the magnetic element is based on the anatomical structure in which the biopsy instrument is to be used. The length depends on the puncture site and the positioning for sample collection in situ. The dimensions of the biopsy instrument can be adapted in a simple and fast manner to the requirements of the different biopsy sites, resulting in savings in time and costs.

Furthermore, it is advantageously provided that between the distal and the proximal portions, the guide element has a receptacle device that serves for receiving the magnetic element. Said receptacle device can involve recesses of different geometrical shapes, comprising polygon, triangle, quadrangle, pentagon, hexagon, heptagon, octagon, nonagon, decagon, ellipse, circle, hyperbola, parabola, superellipse, spherical triangle, cycloide, rosette, helix, sphere, ellipsoid, ellipsoid of rotation, paraboloid, paraboloid of rotation, hyperboloid, oloid or polyeder, or combinations thereof or other shapes. An advantageous embodiment comprises cylindrical, semi-cylindrical, clamp-shaped or film-shaped recesses. These are examples which are not intended to represent a limitation of the receptacle device. Film-shaped in the meaning of the invention means in particular that the receptacle device or the magnetic element is shaped in such a manner that it has a very low thickness and a large area. The magnetic element is preferably shaped according to the shape of the receptacle device. These alternative embodiments too ensure that through the advantageous arrangement of a distally located guide element followed by a magnetic element, a stabilizing element can be connected. Thus, it is achieved that with minimal risk of injury to the patient, the magnetic function of the instrument remains ensured and that after collecting sample material in situ, the biopsy instrument can be entirely removed again from the body from the outside. Furthermore, due to the advantageous embodiment, the biopsy instrument can be adapted to different applications, wherein also due to the shape of the receptacle device or the magnetic element, the amount of samples to be collected varies and can be adapted to the needs of the user. It was a complete surprise that the advantageous embodiment can be placed in an optimal manner at the biopsy sites and that the sampling is not influenced by potentially occurring flow effects so that the samples can be taken without loss.

Advantageously, the magnetic element comprises metal, plastic and/or ceramic materials. Metals comprise, as already listed above, aluminum, beryllium, bismuth, lead, chromium, iron, gold, indium, potassium, copper, magnesium, manganese, molybdenum, sodium, nickel, osmium, palladium, platinum, rhodium, ruthenium, silver, tantalum, titanium, vanadium, tungsten, zinc, tin or zirconium. Ceramic materials are to be understood as a collective term for materials which are crystallized to an extent of more than 30% by volume and are composed of inorganic and predominantly non-metallic compounds or elements. Ceramic materials comprise alumina and kaolin, quartz, feldspar, lime, silimanite, magnesite, terracotta, majolica, faijence raku, paper clay or oxide ceramics. Furthermore, for the advantageous embodiment, plastics can also be used, as already mentioned above in connection with the non-magnetic plastics. The advantageous embodiment ensures that effective and rapid sample enrichment is achieved through the magnetic element and that the collected material is bound to the magnetic element and stays there during the removal of the biopsy instrument. Moreover, through the selection of the material, the risk of injury to the patient is reduced. Increasing the surface of the material is additionally possible in order to additionally increase the effectiveness of sample enrichment. It was found that through the magnetic element, effective sample enrichment is possible, for example, in vessels where a strong flow prevails. This was a complete surprise and represents a significant advantage over the prior art. Due to the preferred magnetic properties of the magnetic element and the non-existing disturbing interactions within a biopsy device of the prior art, it is also possible to enrich samples which are not located in the immediate vicinity of the instrument because the magnetic forces act over a longer distance than antigen-antibody bonding forces. However, the magnetic forces generated by the magnetic element surprisingly did not cause a negative influence on tissues or organs because these forces are weaker than the ones of the magnetic biopsy devices described in the prior art.

In a further advantageous embodiment it is provided that the detection molecules are preferably selected from the group comprising antibodies, antibody fragments synthetic protein scaffolds, peptides, nucleic acids, receptors and/or inorganic materials. Applying detection molecules onto the magnetic element achieves a specific enrichment of samples in situ prior to collection of the sample. The detection molecules can react with cells and/or molecules in the body of humans or animals and bind the cells and molecules. For this, different detection molecules can be used and combined with each other. Through specific positioning of the biopsy instrument in a desired body region and through the specificity and sensitivity of the instrument, it can be achieved that even low concentrations of molecules and/or cells can be detected by the detection molecules. This represents a technical progress. Furthermore, by varying the detection molecules, a broad spectrum of applications is conceivable. It can also be advantageous to apply different detection molecules onto the magnetic element. Thus, for example, different detection molecules can be applied which, for example, are specific to a single or in each case to one particular cell type. This ensures that preferably a specific sample is enriched. The molecules or cells are collected rapidly and efficiently and can then advantageously be quantified and analyzed in a laboratory. In particular, rapid and reliable sample enrichment plays an important role in medicine or, more precisely, in diagnostics for diagnosing diseases.

It is preferred to connect ligands with magnetic nanoparticles. For this, iron oxide particles with different shells can be used. Said particles, which in the meaning of the invention can also be designated as nanoparticles, can be adapted with regard to their size and charge as well as with regard to their magnetic relaxation behavior and also with regard to their magnetic susceptibility and are colloidally stable. The ligands connected with the magnetic nanoparticles bind preferably to defined surface molecules of micro-organisms comprising bacteria, viruses and fungi. Through the decoration with the magnetic nanoparticles, the microorganisms can be rapidly and securely enriched by the magnet element of the biopsy instrument. It can also be preferred to provide a shell material for the magnetic nanoparticles, which said shell material comprises carbohydrates, proteins, nucleic acids and/or polymers and is preferably absorbed by microorganisms. This likewise allows a magnetic decoration of the microorganisms, wherein in particular magnetized microorganisms are created. It was a total surprise that through magnetic decoration of the microorganisms, a magnetic moment can be provided that ensures an undisturbed attraction of the microorganisms in the blood circulation. Through this, it is surprisingly possible in a fast and simple manner to diagnose and/or treat infectious diseases that are associated with microorganisms. Magnetic enrichment advantageously takes place without or in connection with the enrichment through the detection molecules which can also bind to microorganisms. Through this, a twofold bond of the microorganisms can be achieved, which improves the efficiency of sample enrichment significantly. Moreover, in this manner, it is possible to enrich samples even under non-tubular flow conditions. The bond forces of typical ligand-receptor interactions are often not sufficient for isolating target objects of the size of a cell under physiological flow conditions. However, integration of an additional bond vector in the form of the magnetic element makes it possible that also rather large objects can be isolated under physiological flow conditions without creating magnetic interactions within the biopsy instrument or with tissues or organs. Another advantage of the utilization of magnetic attraction forces as functional principle when isolating larger target objects from the blood circulation is based on the fact that these forces usually act over a considerably larger distance than ligand-receptor interactions. However, it was a complete surprise that the magnetic element specifically attracts magnetized target objects, wherein the magnetic biopsy devices described in the prior art have an inaccurate and wide magnetic field accompanied by interactions within the device and with tissues and organs.

Furthermore, it is advantageously provided that the biopsy instrument has an additional covering device. Said covering device preferably has a sheath-shaped structure covering the magnetic element. Other geometric shapes comprising polygon, triangle, quadrangle, pentagon, hexagon, heptagon, octagon, nonagon, decagon, ellipse, circle, hyperbola, parabola, superellipse, spherical triangle, cycloide, rosette, helix, sphere, ellipsoid, ellipsoid of rotation, paraboloid, paraboloid of rotation, hyperboloid, oloid or polyeder can also be used. In this manner, the magnetic element and sample material located there after in situ enrichment can be protected from shearing or deformation prior to removal from the body and contamination outside the body is avoided. An advantageous embodiment is that the covering device is a sliding device which is slid from the proximal portion over the magnetic element. However, other devices comprising folding devices which serve for covering the magnetic element are also conceivable. Through the advantageous embodiment, the enriched sample is protected so that measurement errors are reduced and the quality of the enrichment is improved.

It is advantageous that the covering device preferably covers the magnetic element, wherein the covering device comprises in particular homopolymers, copolymers, biopolymers, chemically modified polymers and/or synthetic polymers. Suitable materials for the covering device are polymer materials comprising polyethylene, polypropylene, polyvinylchloride, polystyrene, polymethylmethacrylate, polyamide, polyester, polycarbonate, polyethylene terephthalate, polyethylene glycol, dendrimers, silicones, proteins, DNA, RNA, carbohydrates or polyhydroxxyalkonates, and preferably polytetrafluorethylene. In particular, if the adjacent components are made from the same material, a good displaceability of the individual components is achieved. Due to the advantageous embodiment, errors during the biopsy are reduced, thereby improving the efficiency and reducing the amount of work.

Another advantageous embodiment is that the biopsy instrument has a longitudinal bore for receiving preferably a mandrin and/or other functional elements. The bore can be implemented in the biopsy instrument using methods known to those skilled in the art, and the width of the bore depends on the application and can vary accordingly. In the thin longitudinal bore channel, e.g., a mandrin (guide wire) can be introduced and pushed forward up to the distal end of the biopsy instrument. In this manner, the rigidity of the instrument can be optimized for placement maneuvers in the body. Also, further functionalizations, e.g. of electronic nature, can be introduced in such a bore in order to increase the usability of the biopsy instrument. The longitudinal bore improves operational safety and constitutes a simplification.

Moreover, configurations of the biopsy instrument are possible that include the following special cases, but are not limited thereto and can be easily performed by a knowledgeable person skilled in the art: arrangement of two or more magnetic sub-elements within the magnetic element preferably with different detection molecules between distal and proximal portions of the guide element; and/or functionalization of the distal portion of the guide element with detection molecules while maintaining the spring-elastic material property of this region. Accordingly, it can be advantageous if the magnetic element comprises one or a plurality of separate or interconnected magnetic sub-elements.

An additional subject matter of the invention is to provide a method for binding microorganisms, the method comprising a biopsy instrument, wherein the method comprises the following steps:
 i. coupling ligands to magnetic nanoparticles;
 ii. binding said ligands to microorganisms;
 iii. binding the magnetic nanoparticles to at least one magnetic element of the biopsy instrument.

Ligands are preferably coupled to magnetic nanoparticles, wherein said ligands are preferably specific to microorganisms. Ligands preferably bind to the surface of microorganisms, whereby the latter are magnetically marked by the magnetic nanoparticles. The magnetic element attracts them once the marked microorganisms are within the range of the magnetic field. With said method, the microorganisms can be magnetically marked or decorated by means of a ligand in a fast and simple manner and can be bound to the magnetic element of the biopsy instrument. This allows, for example, to enrich microbial pathogens from the blood circulation and to determine the resistance pattern. This method is made possible in that bacterial pathogens are decorated in vivo with magnetic nanoparticles and can be enriched with a magnetic element of the biopsy instrument, even under non-tubular flow conditions as they occur in the blood circulation. Advantageously, it is possible to detect pathogens or microorganisms in the blood circulation of patients with sepsis and to perform a faster determination of the resistance profile. In general, pathogen detection and determination of a resistance pattern are a prerequisite for ensuring a targeted and economical antibiotic therapy.

It is preferred that the ligand is oligoacyllisine and/or a glycopeptides antibiotic. The mimetic lipopeptide oligoacyllisin (NC(12)-2-beta(12)), which binds to a broad spectrum of bacteria cells in different media rapidly and with high affinity, is used as a preferred ligand. In contrast to natural peptides, the synthetic oligoacyllisin is not enzymatically degraded and has a half-life in blood of several hours. It is therefore to be used only in low concentrations and is proven not to be toxic or hemolytic. Since oligoacyllysine does not have a bactericidal effect, germs can be isolated alive and can be cultivated in the laboratory. Oligoacyllysine can advantageously be coupled in a chemically covalent manner to magnetic nanoparticles. Another possible ligand belongs to the group of glycopeptide antibiotics, preferably is glycopeptide vancomycin. Vancomycin forms a non-covalent bond with the two terminal D-alanyl-D-analine residues of the amino acid chain of the cell wall's basic components (N-acetylglucosamine-N-acetylmuramic acid-pentapeptide). It binds with high avidity to Gram-positive bacteria and with a slightly lower avidity also to Gram-negative germs. It is surprisingly possible to decorate microorganisms by means of the ligand, wherein said microorganisms become also magnetic through the covalently bound magnetic nanoparticles. This enables a bonding and an enrichment of such decorated microorganisms by means of the magnetic element of the biopsy instrument. It was a complete surprise that the magnetic element does not have the disadvantages and shortcomings of the biopsy devices described in the prior art, which are completely magnetic. It was found that the biopsy can be designed smaller so that it reaches areas which previously were not accessible for a biopsy device. Thus, it is possible with the preferred biopsy instrument to detect, enrich and isolate microbial pathogens or microorganisms which are present in the case of a sepsis, for example.

It is readily apparent for the person skilled in the art that magnetic particles can also be configured with other ligands which can be selected from the group comprising antibodies, antibody fragments, synthetic protein scaffolds, peptides, nucleic acids, receptors and/or inorganic materials in order to mark other target object within the body in order to be subsequently enriched in the body with the aid of the magnetic biopsy instrument and to be subsequently obtainable from the body for further purposes. Examples for this are markings of tumor cells, trophoblasts, biomarkers or other low concentrated cell populations or molecules.

Furthermore, it is a subject matter of the invention to provide a biopsy kit for the enrichment of sample material from different body regions and body cavity systems, and the use of said kit. The biopsy kit comprises at least the following components of the biopsy instrument:

i. a guide element, comprising a spring elastic distal portion and a proximal portion,
ii. one or a plurality of magnetic elements which are fitted between the distal and the proximal portions of the guide element, wherein detection molecules are applied on the surface of at least one magnetic element, and
iii. a stabilizing element that is connected to the proximal portion of the guide element, wherein the guide element, the magnetic element and the stabilizing element are arranged sequentially from distal to proximal.

The biopsy kit comprises at least one guide element, a magnetic element and a stabilizing element, wherein the magnetic element and the stabilizing element are arranged sequentially from distal to proximal. The guide element has a distal and a proximal portion, and the distal portion is configured in a spring-elastic manner. It can also be advantageous to construct special forms of the biopsy instrument, in which the magnetic element comprises two or more magnetic sub-elements with different detection molecules and is arranged between the distal and the proximal portions of the guide element. It can also be preferred to provide at least one magnetic element without detection molecules. Advantageously, the functionalization of the distal portion of the guide element can be carried out with detection molecules, and the spring-elastic material properties of this region can be maintained. The biopsy kit can be supplemented with specific components which preferably facilitate the use for specific biopsy sites (for example in the blood vessel system or in the urogenital apparatus) or allow the use by utilizing other auxiliary medical devices (e.g. rigid or flexible endoscopes).

The risk of injury to the patient during the biopsy is reduced by the biopsy kit or, more precisely, by the configuration of the biopsy kit. In particular, the spring-elastic distal portion of the guide element ensures that upon contact with a surface such as, e.g., a vessel wall or an organ, no damage to the biological material occurs. As soon as the pressure on the surface is too high, the spring-elastic guide element deforms, thereby reducing the pressure on the surface.

Between the distal and the proximal portion of the guide element, at least one magnetic element is attached which serves in particular for magnetically binding magnetic nanoparticles, magnetized microorganisms or magnetized ligands. Thus, due to special configuration of the magnetic element, an enrichment of special cells or molecules, preferably microbial pathogens, can take place in the body of humans and animals, i.e., in situ, which is a movement away from the usual technology and solves a long-standing problem of the prior art. Due to the high specifity of the magnetic element, a rapid enrichment of sample material is achieved, whereby the patient is treated gently and relieved from stress. Moreover, the enrichment can take place in systems that are characterized by a strong flow.

Furthermore, a stabilizing element is connected to the proximal portion of the guide element. The stabilizing element serves for fixing the magnetic element during the biopsy and thus prevents dislocation of said magnetic element. In this manner, it is achieved that the biopsy instrument is removed as a whole from the body of the patient, i.e., no component of the biopsy instrument interacts with the surfaces in such a manner that damage is caused to the surfaces, and no components of the instrument remain in the body regions. Advantages of the biopsy kit according to the invention are the accuracy with which the instrument can be positioned in body regions and the specifity and sensitivity with which cells and molecules can be enriched in situ. In particular, magnetized microorganisms can be enriched which are potentially associated with a disease. The biopsy kit can be easily operated by a person skilled in the art and reduces the risk of injury to the patient. Further advantages are the low costs of the biopsy kit and a high degree of flexibility in terms of the configuration for different biopsy sites and applications, even when using additional auxiliary means such as, e.g., endoscopes. Furthermore, a rapid and reliable enrichment of samples for diagnosing diseases is an important criterion.

A biopsy kit is provided with which it is possible to position the components necessary for sample enrichment, to keep them stationary in the body for the time needed for enriching the specific sample material, and to remove them entirely together with the collected sample material after the dwell time. For correct positioning for sample collection and for the successful removal procedure of the sample material from the body, visual or other guide markings are used on the components of the biopsy kit, which can be implemented through engraving, colored or tactile or signaling marks, and which allow finding a geographical position of the biopsy instrument during positioning and sampling within the body and during the process of removing the biopsy instrument from the body. The positioning of the biopsy instrument can be ensured in situ by means of imaging methods. Fort this, known contrast agents can be used on the construction side by the person skilled in the art. Also, the biopsy kit can be adapted for specific biopsy sites with regard to the dimensions of the individual components and can be supplemented with auxiliary means in order to make components available during the biopsy that are necessary or desirable for special applications. Furthermore, the biopsy kit can be provided as a disposable item, which better meets the hygienic requirements in medical facilities.

The biopsy kit can be advantageously used to remove samples, preferably from the blood vascular system including the ventricles, the pulmonary and systemic circulation and the arterial and venous system as special biopsy sites, the gastrointestinal tract, wherein the biopsy instrument can be optionally positioned from the oral or anal direction, from the efferent glandular ducts of the pancreas, lachrymal gland, parodit gland, from the efferent ducts of the mucosal glands, mixed glands and cutaneous and sebaceous glands including the mammary gland, from the spinal canal or brain chamber system, from the gall bladder and its efferent anatomical structures, from the efferent urinary tracts or the lymphatic system, or can be used for taking samples from the body cavities of the abdomen or the chest, the uterus, the urogenital apparatus or a joint space.

A flexible design of the biopsy kit allows the enrichment of samples in different systems. A preferred field of use is the vascular system of the body. In this case, the biopsy kit is positioned in the vascular system via a vascular indwell cannula. Further fields of use comprise the gastrointestinal tract, the efferent bile ducts, the pancreatic duct or the efferent urinary tracts. While for the use in the vascular system, the outer diameter of the biopsy kit is based on the diameter of the blood vessel, the length depends on the puncture site and the positioning for sample connection in situ. The outer diameter can be adjusted accordingly for placement in the pancreatic duct, bile duct, cystic duct, or the efferent urinary tract, or the bladder, or the peritoneum, or the tracheobronchial tree, or the pleural cavity or a joint space. The advantageous embodiment and dimensioning can thus be carried out through quick and simple adaptations by a person skilled in the art. Accordingly, it solves a long-standing problem in the prior art and provides a fast and specific embodiment that can preferably be used in different body regions, preferably in body cavity systems, and does not have the disadvantages of the prior art.

Descriptions of the embodiments of the biopsy kit are exemplary for cases of applications using an endoscope, and for sample enrichment and sample removal from the vascular system as the main cases of application; however, the composition of the biopsy kit is not limited to these individual cases but can be modified or supplemented for other applications by a knowledgeable person skilled in the art.

The use of a biopsy kit is advantageous if the biopsy instrument is placed via auxiliary endoscopic means, preferably a gastroduodenoscope, cystoscope, urteroscope, rectoscope, proctoscope, coloscope, arthroscope, laparascope, colposcope, hysteroscope, ophthalmoscope, laryngoscope and/or bronchoscope. An endoscope in the meaning of the invention is a device with which the interior of living or dead organisms can be examined or manipulated. For the use of the biopsy instrument via an endoscope, the following elements are advantageous as components for the biopsy kit:
  i. a guide element comprising a spring-elastic distal and proximal portion and a proximal portion,
  ii. magnetic elements having one or a plurality of detection elements, said magnetic elements being arranged between the distal and the proximal portions of the guide element,
  iii. a stabilizing element connected to the proximal portion of the guide element,
  iv. an adaptor that allows inserting the biopsy instrument via the working channel of the endoscope and/or
  v. a transparent and longitudinally displaceable sheath that can be attached on the adaptor, surrounds the biopsy instrument outside the body and ensures hygienic handling during its dwell time in the body.

The length of the entire biopsy kit comprising the guide element, the magnetic element and the stabilizing element is to be selected in such a manner that after endoscopic placement, the endoscope can be removed from the body, usually via the instrument channel of the endoscope, without changing the position of the biopsy kit. This can be achieved in that the total length of the biopsy kit is adapted to the total length of the endoscope. A knowledgeable person skilled in the art is readily capable to construct special forms of the biopsy instrument in which the magnetic element comprises two or more magnetic sub-elements with different detection molecules and is arranged between the distal and the proximal portions of the guide element, or in which the functionalization of the distal portion of the guide element is to be carried out with detection molecules while maintaining the spring-elastic properties of this region.

The use of a biopsy kit is advantageous if the biopsy kit is inserted into a vascular system through a vascular access. Here, the detection molecules placed on the magnetic element can detect different molecules and/or cells in the vascular system. For the use of the biopsy kit via a vascular access, the following components are useful as further components of the biopsy kit:
  i. an indwelling vascular cannula with puncture needle;
  ii. an adapter that can be attached to the indwelling vascular cannula and via which the biopsy instrument can be intravascularly positioned;
  iii. a port that is preferably implemented on the adapter and via which an infusion solution can be applied during the dwell time of the biopsy instrument in the body, and/or
  iv. a transparent and displaceable sheath that can be slid onto the adaptor, surrounds the biopsy instrument outside the body and ensures hygienic handling during its dwell time in the body.

With the advantageous embodiment, sample enrichment with a high yield can be achieved quickly and efficiently if the biopsy kit is inserted into a vascular system via a vascular access. This applies in particular in the case if said kit comprises all mentioned components. The collected sample can be analyzed immediately after extraction from the vascular system or can be transferred to adequate processing locations. The embodiment thus represents a significant reduction of workload for hospital staff.

In a very similar manner, the biopsy kit can be used for enriching and collecting sample material from the spinal canal and the epidural space if instead of the indwelling vascular cannula, a spinal puncture cannula or a cannula for puncture of the epidural space is utilized as it is used, for example, in epidural anesthesia.

In addition to placement via an indwelling vascular cannula and via an endoscope, placement in the course of a surgical intervention or in the course of a minimal invasive surgical procedure is also advantageous which, with regard to the dimensions of the biopsy instrument, advantageously does not impose additional requirements other than the ones already mentioned. The advantageous embodiment results in an improvement in quality and an increase in reliability of sample enrichment.

It is preferred that the biopsy instrument and/or the kit is used for enriching samples and the samples are preferably used for diagnosis, in particular prenatal diagnosis, cancer diagnosis, for therapy follow-up (point-of-care diagnostics) and/or for diagnosis of homoeostasis in patients. Furthermore, the biopsy instrument can advantageously be used for the diagnosis of a disease selected from the group comprising inherited diseases, proliferative diseases, inflammatory diseases, autoimmune diseases, infectious diseases, hormonal disorders, diseases of blood and blood-forming organs, diseases of the digestive tract, liver, bile, pancreas, diseases of the urogenital tract and kidney, diseases of the heart, abnormal changes in the vascular system and lymphatic system, pulmonary diseases, diseases of the central or peripheral nervous system and electrical stimulus transmission, and neurodegenerative diseases. The biopsy instrument advantageously collects samples that can be used for diagnosing the mentioned diseases, that is, the biopsy instrument and the method implemented with said instrument serve for obtaining an intermediate step on the way to diagnostic results. The diagnosis instrument can thus be used for diagnosing different diseases. Surprisingly, the biopsy instrument can be used for diagnosis or obtaining an intermediate step on the way to diagnostic results and/or for monitoring the therapy progress of the following diseases:
  Heriditary diseases, preferably comprising autosomal recessive, autosomal dominant, gonosomal and mitochondrial or extrachromosomal hereditary disease and/ or any disease that can be attributed to a genetic disposition. Proliferative diseases comprise preferably tumors, precancerosis, dysplasia, neuroendocrine tumors, endometriosis and/or metaplasia.

Autoimmune diseases, preferably comprising rheumatoid arthritis, inflammatory bowel disease, osteoarthritis, neuropathic pain, alopecia greata, psoriasis, psoriatic arthritis, acute pancreatitis, allograft rejection, allergies, allergic inflammations of the lung, multiple sclerosis, Alzheimer's disease, Crohn's disease, and/or systemic lupus erythematous.

Infectious diseases, preferably comprising infections caused by parasitic disease, bacterial disease and/or viral diseases. It was a complete surprise that by means of the biopsy instrument, microorganisms can be collected rapidly and securely and can also be identified. Here, the microorganisms are preferably identified by ligands which are coupled to magnetic nanoparticles, wherein the ligands bind to the microorganisms. In this manner, the microorganisms are magnetically decorated and can be bound by means of the magnetic element of the biopsy instrument.

Hormonal diseases, preferably comprising diseases of sugar metabolism, lipid metabolism, protein metabolism, sexual development and reproduction, water-salt balance, growth and/or cell formation.

The dwell time of the biopsy instrument in the body regions can preferably be varied and depends on the present concentrations of the material to be enriched. The biopsy instrument can be positioned in the body regions in such a manner that a specific enrichment is possible. By means of the magnetic element, certain microorganisms, which preferably are marked with magnetic nanoparticles or other magnetic elements, can be detected and/or isolated in a simple and fast manner. This represents a step forward since in this manner, rapid and reliable diagnosis and therapy follow-up is possible. After enrichment of the sample, the magnetic element can preferably be covered by means of a covering device, thereby preventing loss of the sample during removal from the body and preventing contamination outside the body. By using the biopsy instrument errors during sampling are prevented and high specifity is ensured. Furthermore, it can be used for enriching samples that are present in low concentrations in body regions that are difficult to access.

Due to the simple and fast replacement of the magnetic element or the detection molecules of the magnetic element, the biopsy instrument can be used for diagnostics in different medical fields. Specifically in prenatal and tumor diagnostics, a fast and reliable diagnosis is crucial. When detected early enough, diseases such as heart defects, spina bifida and cleft lip and palate can be treated. Thus, the use of the biopsy instrument with the appropriate detection molecules offers the possibility to enrich samples and to analyze them for diseases and to monitor, examine and, if necessary, change the effect of a chosen therapy. Likewise, in the field of cancer diagnosis, a fast and reliable detection is absolutely necessary in order to start, monitor and, if necessary, adjust therapeutic treatment as early as possible. However, this requires that the tumor is identified. The use of the biopsy instrument offers the possibility of cancer markers that are characteristic for certain types of tumors to be enriched in body regions, e.g., the vascular system or efferent glandular ducts, thereby enabling a fast diagnosis and therapy follow-up.

Advantageously, the biopsy instrument can be used for therapy follow-up, which means that samples are collected with the biopsy instrument, are analyzed and used for monitoring the therapy progress. The latter comprises, for example, monitoring of tumor treatment, monitoring of an autologous, syngeneic, allogenic, xenogenic or alloplastic transplantation, monitoring of an inflammatory disease, monitoring of an infectious disease, monitoring of a hormonal disorder, monitoring of a psychiatric disorder, and/or monitoring of a neurodegenerative disease. Surprisingly, the biopsy instrument can be easily and reliably adapted to the diagnosis of various diseases. For example, the magnetic element can be provided with capture structures. In the meaning of the invention, the capture structures can also be designated as detection molecules. A person skilled in the art is familiar with these capture structures, which also allows to evaluate the collected samples preferably in an automated manner. Accordingly, the samples are evaluated within a short time and the collected data can be advantageously used to decide on further treatment.

Particularly advantageous, the instrument can be used for primary diagnosis, diagnosis of tumor spread or tumor grading. Advantageously, samples can be taken over an extended period and at regular time intervals from patients at risk in order to possibly detect the development of a tumor at an early stage. For example, the collected biopsy samples can be analyzed and evaluated by a laboratory. However, the instrument can be used not only for primary diagnosis, but also for long-term monitoring of tumor spread. For example, tumor growth or metastasis formation of a tumor can be monitored. These data in connection with, for example, the degree of differentiation (tumor grading) of the tumor advantageously provide the attending physician with important information which can be crucial for the further progress of the treatment. Advantageously, the collected samples can be analyzed fast and reliably, which is essential for successful treatment.

Advantageously, the biopsy instrument can be used for prenatal diagnosis. Here, the samples are collected and preferably examined for gene mutations, chromosome mutations and chromosome abberations from the group comprising deletion, inversion, duplication, translocation, ring chromosomes, and/or a malfunction of gene transcription, gene translation, mRNA stability, of a splice variant, a malfunction of the mRNA transport into the cytoplasm, of the protein biosynthesis and/or an epigenetic factor. Advantageously, detection molecules, so-called capture molecules, can be applied onto the surface of one or a plurality of magnetic elements. The molecules are preferably specific to the samples to be detected which can likewise be marked with magnetic nanoparticles. For example, the collected samples can be further analyzed in a laboratory and forwarded to an attending physician. Advantageously, by enriching preferably only specific samples, the analysis is significantly simplified and can be performed within a short time. The biopsy instrument not only allows a faster analysis, but also improves the quality of the samples. Preferably, specific samples are collected which are advantageously protected against dislocation when removing the instrument from the body.

Furthermore, the biopsy instrument can be used to monitor the homoeostasis of patients. Especially in the case of serious illnesses or after surgical interventions using instruments, continuous monitoring of the patient's condition is necessary. For this purpose, the biopsy instrument can be used universally and can advantageously be adapted to the different requirements in a simple, fast and cost-effective manner.

Further advantages of the biopsy instrument according to the invention are: cost reduction, simplification, savings in time, material, work steps and in costs or raw materials that are difficult to find, increased reliability, elimination of errors, quality improvement, no maintenance, higher effectiveness, higher yield, more technical possibilities, opening a new field, achieving an object for the first time, potential for rationalization and/or miniaturization.

The invention is explained in more detail hereinafter by means of an example without being limited to said example.

Determining Dimensions and Selection of Magnetic Materials for Producing Calibration Magnets and Characterization of their Magnetic Properties Magnets can be dimensioned and constructed as desired. However, the anatomic conditions within the body are limiting. Since in one preferred embodiment, miniaturized fixed magnets are used which have sufficient attractive force, calibration magnets from different magnetic materials (e.g. neodymium, samarium cobalt) are prepared. Furthermore, it is also possible to use electromagnets which can be adapted through their dimension to anatomic conditions within the body and which have the advantage that their magnetic field can be switched on and off.

Identification of Ligands and Coupling the Same to Magnetic Nanoparticles

The mimetic lipopeptide oligoacyllisin (NC(12)-2-beta (12)), which binds a broad spectrum of bacteria cells in different media rapidly and with high affinity, is used as a preferred ligand. In contrast to natural peptides, the synthetic oligoacyllisin is not enzymatically degraded and has a half-life in blood of several hours. It is therefore to be used only in low concentrations and is proven not to be toxic or hemolytic. Since oligoacyllysine does not have a bactericidal effect, germs can be isolated alive and can be cultivated in the laboratory. Oligoacyllysine can advantageously be coupled in a chemically covalent manner to magnetic nanoparticles. Another possible ligand belongs to the group of glycopeptide antibiotics, preferably is glycopeptide vancomycin. Vancomycin forms a non-covalent bond with the two terminal D-alanyl-D-analine residues of the amino acid chain of the cell wall's basic components (N-acetylglucosamine-N-acetylmuramic acid-pentapeptide). It binds in particular with high avidity to Gram-positive bacteria and with a slightly lower avidity also to Gram-negative germs.

As a negative control for the two ligand-coupled and thus functionalized nanoparticles, preferably, dextran-covered nanoparticles can be used which have no functionalization.

Magnetic Nanoparticles

Differently sized iron oxide particles with different shells can be used and can be equipped with different ligands. One particle type is also particularly suitable for magnetic particle imaging. This particle type is preferably used for ligand coupling. The particles can be characterized with regard to size and charge, wherein the magnetic relaxation behavior and the magnetic susceptibility can be determined and the colloidal stability can be checked.

Nanoparticle Production and Functionalization

The synthesis protocols for producing magnetic nanoparticles can comprise precipitation methods in aqueous solution or also association reactions in organic solvents. The sheath material can be applied simultaneously or sequentially. The ligand coupling to functional groups of the particle sheath can take place via carboxyl, amino, thiol binding sites or other binding sites common in biochemistry, but can also be carried out via click reactions which utilize non-natural amino acids in order to optimize selected ligands for the decoration of model bacteria.

Identification, Cultivation and Characterization of Clinically Relevant Model Bacteria In order to test the principle of operation of the biopsy instrument, for example, the following bacteria can be used: *E. coli* (DSMZ-no. 1103, ATCC-no. 25922); *staphylococcus aureus* (DSMZ-no 20231, ATCC-no. 12600). These strains are cultivated and characterized with the usual microbiological methods.

Magnetotactic Bacteria

Magnetotactic bacteria can also be used as naturally occurring magnetic "calibration bacteria" in an artificial circulation system in order to test the function of the biopsy instrument. These bacteria synthesize intracellular magnetic nanoparticles, so-called magnetosomes, which generate strong magnetic dipoles which function as biological compass needles.

Magnetotactic bacteria are available, for example, from DSMZ (e.g. magnetospirillum magnetotacticum, DSMZ-no. 3856, MS-1, ATCC-no. 31632) and can be cultivated in liquid medium 380. First, these bacteria can be characterized with regard to their magnetic properties so as to obtain reference values about the binding capacity of the bacteria on the magnet. Through the ferrozine test, for example, the iron content per bacteria cell can be quantitatively determined. By means of magnetorelaxometry, the magnetic behavior of the bacteria can be measured.

Magnetic Separation

The binding efficiency of nanoparticles functionalized with ligands on model bacteria can be examined with the aid of magnet separation. For this, model bacteria can be incubated with the functionalized nanoparticles and then be cleaned through a magnetic column. With this method, magnetically decorated bacteria can be separated from non-decorated ones.

Circulation System

For testing the biopsy instrument, a physiological circulation system is available in which a pulsatile flow profile in differently calibrated tubes with different elastic behavior can be achieved. In this manner, flow conditions as they exist at different anatomic sites of the blood circulation system can be simulated.

Examinations in a Circulation System

For this purpose, magnetotactic bacteria, which were previously characterized, are administered in a physiological in vitro model of the blood circulation system. By means of differently dimensioned miniaturized calibration magnets with known magnetic properties (remanence and coercive force), said bacteria can be enriched and isolated under physiological flow conditions. Here, the bacteria concentration in the medium as well as the dwell times of the calibration magnet can be varied. In a first test setup, a physiological buffer solution is used in the circulation system. In a second test setup, the magnetic "calibration bacteria" are inoculated in coagulation-inhibited whole blood and are likewise isolated from the artificial circulation system with miniaturized calibration magnets and are quantified.

The fact that bacteria can be isolated from the blood circulation by means of the preferred biopsy method, which uses magnetic elements, can be shown in the following experiment in two stages:

Stage 1: Functionalized magnetic nanoparticles can be incubated with bacteria in a test tube, administered in a circulation system, and isolated using a calibration magnet.

Stage 2: First, bacteria are administered into a circulation system and then, functionalized magnetic nanoparticles are administered. Subsequently, a calibration magnet is introduced into the circulation system and checked in defined time intervals for isolation of model bacteria.

This experiment can be carried out in a physiological buffer solution and in coagulation-inhibited whole blood as a flowing solution for the circulation system. The concentration of magnetically decorated model bacteria in a physiological circulation necessary for the isolation with a miniaturized calibration magnet model is known. The time period within the calibration magnet has to be deposited in the circulation system so as to enable effective bacteria isolation is also known.

Experiment In Vivo

The model bacteria classified as being clinically relevant were intravenously administered in a defined number (106 to 108 cfu) in rats. Subsequently, functionalized magnetic nanoparticles were injected into the circulation and the insulation of model bacteria was checked after defined time intervals.

Figure 2:
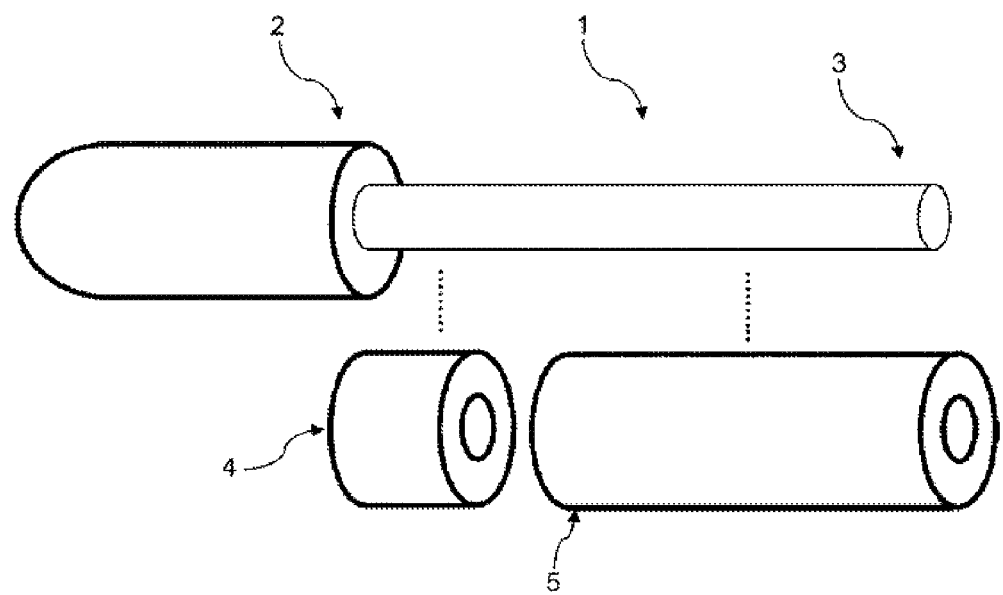
Figure 3:
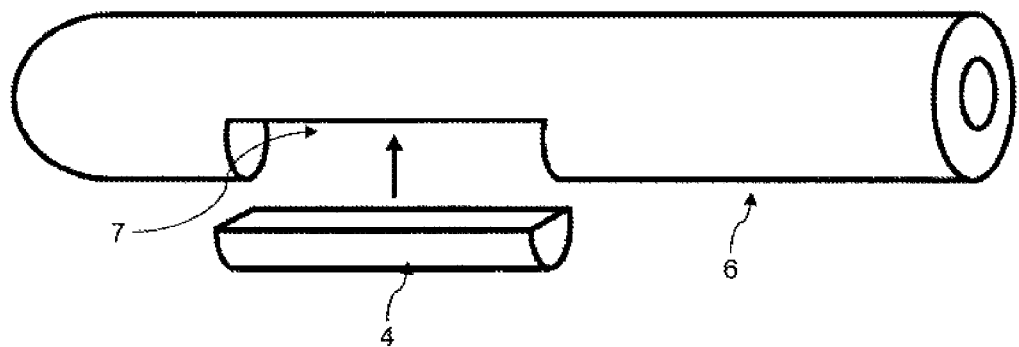
Figure 4:
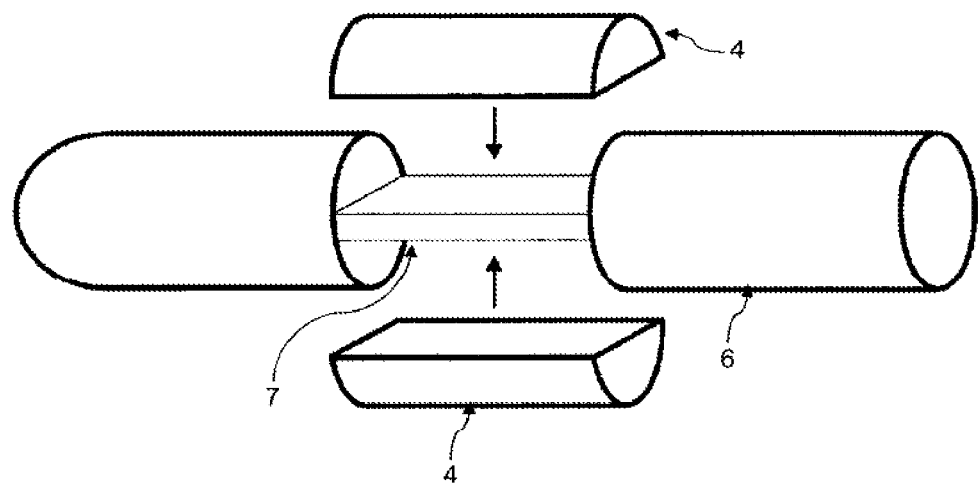
Figure 5:
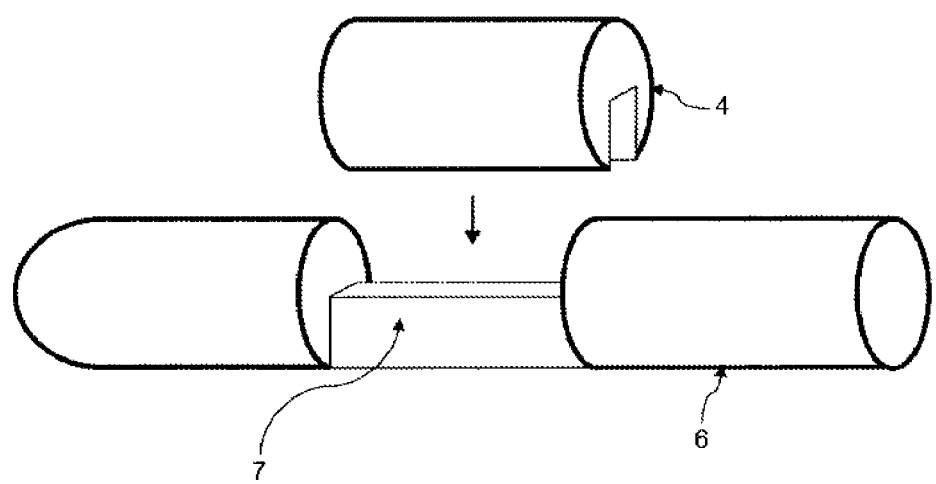
Figure 6:
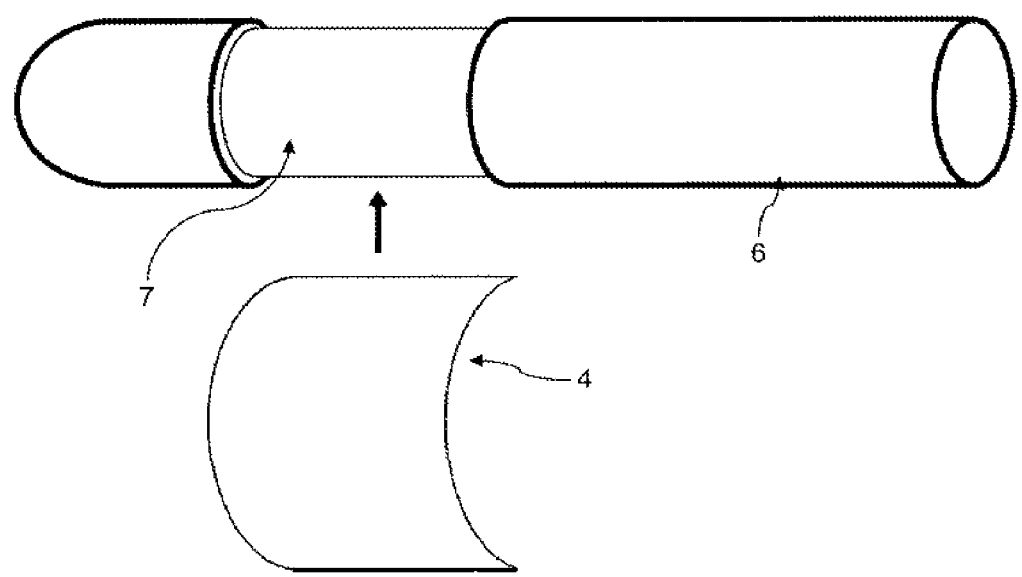
Figure 7:
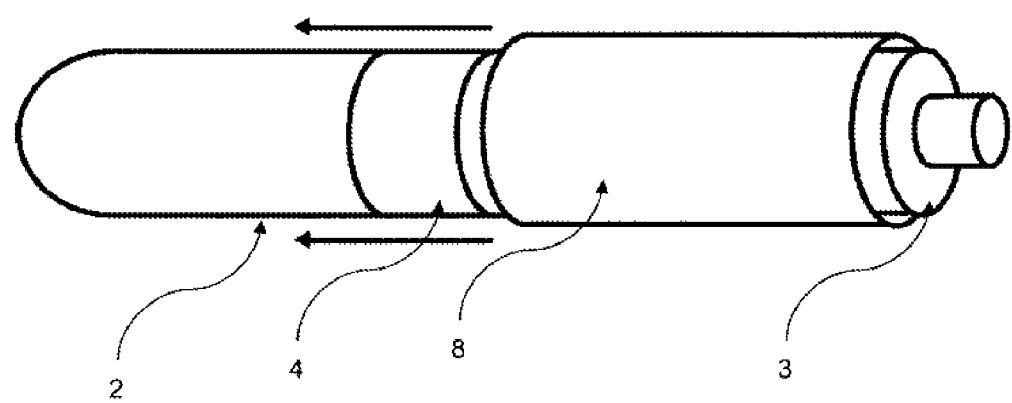
Figure 8:
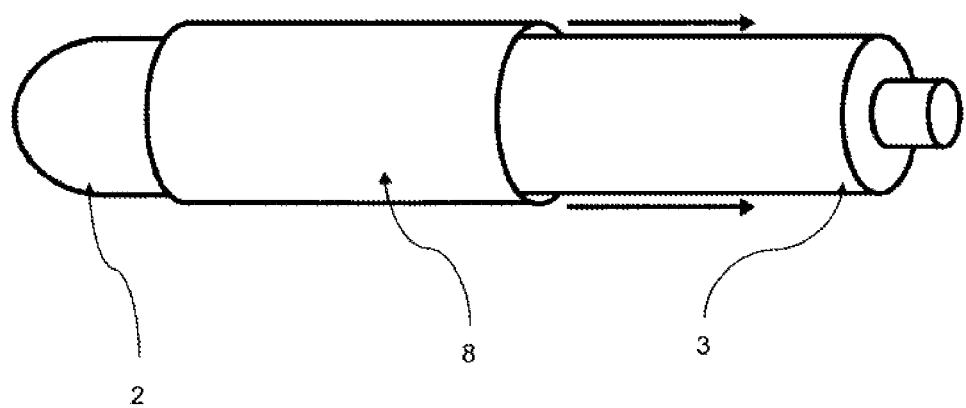

The invention is now exemplary described by means of figures without being limited thereto. In the figures:

FIG. 1 shows a side view of a guide element with a distal and a proximal portion, FIG. 2 shows a side view of a guide element with a cylindrical magnetic element and a cylindrical stabilizing element, FIG. 3 shows a side view of a biopsy instrument with a receptacle device for a semi-cylindrical magnetic element, FIG. 4 shows a side view of a biopsy instrument with a receptacle device for two semi-cylindrical magnetic elements, FIG. 5 shows a side view of a biopsy instrument with a strut-shaped receptacle device for a clamp-shaped magnetic element, FIG. 6 shows a side view of a biopsy instrument with a receptacle device for a film-shaped magnetic element, FIG. 7 shows a side view of a biopsy instrument with a covering device, and FIG. 8 shows a side view of a biopsy instrument with a covering device over a magnetic element.

FIG. 1 shows a schematic side view of a guide element. The guide element 1 consists of a distal 2 and a proximal 3 portion. The distal portion 2 of the guide element 1 is configured in a spring-elastic manner. It can be made from metals, preferably steel. Alternatively, for this component, non-metallic materials can also be used which can be formed into thin cylindrical structures. Polymer materials such as, e.g., polytetrafluoroethylene are possible here. The distal portion 2 of the guide element 1 is firmly connected to the proximal portion 3. However, the distal 2 and proximal portions 3 of the guide element 1 can be manufactured using one manufacturing process if the material permits this, e.g., by using suitable plastics for the production.

FIG. 2 shows a schematic side view of a guide element with a magnetic element and a stabilizing element. The magnetic element 4 in FIG. 2 can additionally carry detection molecules on its surface, wherein said detection molecules react with specific cells and/or molecules in the body of humans and animals and thereby permit an improved enrichment of sample material in situ prior to removal from the body. The configuration of this element is substantially to be implemented as a cylindrical hollow body which is dimensioned with regard to its size in such a manner that it can be fitted from the proximal portion 3 onto the guide element 1. For this, the inner diameter of this component is larger than the outer diameter of the proximal portion 3 of the guide element 1. In relation to the distal portion 2 of the guide element 1, the outer diameter of the magnetic element 4 can be larger, equal or smaller. However, the outer diameter of the magnetic element 4 is preferably 0.01 to 0.1 mm smaller than the outer diameter of the distal portion 2 of the guide element 1. Materials for producing this component comprise metals, plastics or ceramic materials which can serve as a substrate for anchoring detection molecules. A configuration in the form of tiny hollow fibers or sponges is also possible.

Furthermore, a stabilizing element 5 is illustrated in FIG. 2. This component is characterized in that it is tubular and can be fitted precisely onto the proximal portion 3 of the guide element 1. The outer diameter of the stabilizing element 5 corresponds to the outer diameter of the distal portion 2 of the guide element 1. The wall thickness of this tubular element is dimensioned such that the magnetic element 4 is slip-resistantly fixed on the guide element 1 by the stabilizing element 5. For this purpose, the stabilizing element 5 and the proximal portion 3 of the guide element 1 can enter into a stable connection, which can be readily implemented without a functional loss, e.g., in a mechanical manner by adhesive bonding or welding at the proximal end of the biopsy instrument. Furthermore, it is advantageous if the two components are reversibly connected to each other. In this manner, it can be ensured that after successful sample enrichment, the magnetic element can be removed from the biopsy instrument and sent to adequate laboratories for performing subsequent diagnosis methods. By using materials for the stabilizing element which give said stabilizing element rubber-elastic properties, it is possible to produce biopsy instruments which can be optimally placed at different biopsy sites in the body.

FIG. 3 shows a side view of a biopsy instrument with a receptacle device for a semi-cylindrical magnetic element. The guide element 1 and the stabilizing element 5 can be produced using one manufacturing method and, accordingly, can be permanently connected. The guide element/stabilizing element 6 produced in this manner has a receptacle device 7 that serves for receiving a magnetic element 4. The form of the receptacle device 7 can have different shapes such as, e.g., the shape of a half-cylinder. The magnetic element 4 is shaped according to the receptacle device 7. This allows varying the samples to be collected, or quickly and easily exchanging the magnetic element 4 in order to adapt it to new situations.

FIG. 4 illustrates a side view of a biopsy instrument with a receptacle device for two semi-cylindrical magnetic elements. The biopsy instrument can be configured such that the guide element 1 and the stabilizing element 5 of FIG. 2 are manufactured using one manufacturing process resulting in a guide element/stabilizing element 6 and a receptacle device 7 in which two magnetic elements 4 can be inserted. Here, the receptacle device 7 can be configured such that two semi-cylindrical magnetic elements 4 can be inserted therein. Onto the two magnetic elements 4, different detection molecules can be applied which, as a result, allow or improve the enrichment of different cells and/or molecules. Furthermore, through such a configuration, the yield of the sample can be increased.

FIG. 5 shows a side view of a biopsy instrument with a strut-shaped receptacle device for a clamp-shaped magnetic element. The receptacle device 7 can be configured such that it is strut-shaped and accordingly, can receive a clamp-shaped magnetic element 4. The magnetic element 4 configured in this manner can be replaced quickly. In this embodiment alternative too, a magnetic element 4 is arranged between a distal portion 2 and a proximal stabilizing element 5. It is achieved here that at a minimal risk of injury to the patient, the biofunction of the instrument remains ensured and that after collecting sample material in situ, the biopsy instrument can be entirely removed again from the body from the outside.

FIG. 6 shows a side view of a biopsy instrument with a receptacle device for a film-shaped magnetic element. For applications requiring the reduction of the outer diameter of the biopsy instrument, a film-shaped receptacle device 7 can serve for receiving a film-shaped magnetic element 4. In the meaning of the invention, a film-shaped magnetic element refers to a shape with a very small thickness and a large area. This embodiment can be used in particular in small vessels in which samples have to be enriched. Moreover, special detection molecules in the form of an inorganic material with which the enrichment of certain organic and/or inorganic molecules can be achieved can also be introduced in this manner into the receptacle device 7. Thus, the biopsy instrument can serve for enriching cells and/or molecules present in low concentrations in regions of the body.

FIG. 7 shows a side view of a biopsy instrument with a covering device. Here, a covering device 8 is shown which can comprise a sheath-shaped structure and slides on the biopsy instrument. Said covering device 8 is fitted from the proximal portion of the guide element onto the biopsy instrument. Suitable materials for the covering device 8 are polymers, preferably polytetrafluoroethylene. In particular, if the adjacent components are made from the same material, a good displaceability of the individual components is achieved.

FIG. 8 illustrates a side view of a biopsy instrument with a covering device over a magnetic element. Here, the covering device 8 is fitted on the guide element/stabilizing element and serves for covering the magnetic element 4. After enrichment of the samples, the covering device is slid in the distal direction over the magnetic element 4, whereby the magnetic element 4 and the enriched sample material are protected during retraction of the biopsy instrument from the body regions, and contamination is avoided. Therefore, high quality and yield can be achieved.

REFERENCE LIST

1 Guide element
2 Distal portion
3 Proximal portion
4 Magnetic element
5 Stabilizing element
6 Guide element/stabilizing element
7 Receptacle device
8 Covering device

The invention claimed is:

1. A biopsy instrument for the enrichment of sample material, comprising:
   i. a non-magnetic guide element comprising a spring-elastic distal most portion of the guide element and a proximal portion,
   ii. a magnetic element having a first end and a second end that is fitted between the distal portion and the proximal portion of the guide element, and
   iii. a non-magnetic stabilizing element connected to the proximal portion of the guide element,
   wherein the first end of the magnetic element directly abuts the spring-elastic distal portion of the guide element and the second end of the magnetic element directly abuts the stabilizing element, wherein the biopsy instrument is configured for the enrichment of the sample material and for insertion into a body of a subject, and
   wherein the stabilizing element is configured to stabilize the magnetic element during a biopsy and to avoid dislocation of the magnetic element and the stabilizing element being
   a. adhesively bonded and/or welded to the proximal portion of the guide element, or
   b. adapted to be slid over the proximal portion of the guide element.

2. The biopsy instrument according to claim 1, wherein the distal portion of the guide element, the magnetic element and the stabilizing element are arranged sequentially from distal to proximal.

3. The biopsy instrument according to claim 1, wherein the stabilizing element is cylindrical.

4. The biopsy instrument according to claim 1, wherein the outer diameter of the stabilizing element is equal to the outer diameter of the distal portion of the guide element.

5. The biopsy instrument according to claim 1, wherein the stabilizing element is reversibly connected to the proximal portion of the guide element.

6. The biopsy instrument according to claim 1, wherein the stabilizing element is made of plastic.

7. The biopsy instrument according to claim 1, wherein the guide element and the stabilizing element are fabricated using one manufacturing process.

8. The biopsy instrument according to claim 1, wherein the magnetic element has a cylindrical shape.

9. The biopsy instrument according to claim 1, wherein the magnetic element has an outer diameter that is smaller than the outer diameter of the distal portion of the guide element.

10. The biopsy instrument according to claim 1, wherein the magnetic element is additionally equipped with detection molecules.

11. The biopsy instrument according to claim 1, wherein between the distal and the proximal portions, the guide element has a receptacle device that serves for receiving the magnetic element.

12. The biopsy instrument according to claim 1, wherein the magnetic element contains magnetic materials and may comprise metal, plastic and/or ceramic materials, or is an electromagnet.

13. The biopsy instrument according to claim 1, wherein the detection molecules are selected from the group comprising antibodies, antibody fragments, protein scaffolds, peptides, nucleic acids, receptors and/or are inorganic materials.

14. The biopsy instrument according to claim 1, wherein the spring-elastic distal portion of the guide element comprises detection molecules.

15. The biopsy instrument according to claim 1, wherein the biopsy instrument further comprises a covering device.

16. The biopsy instrument according to claim 15, wherein the covering device covers the magnetic element, and wherein the covering device comprises homopolymers, copolymers, biopolymers, chemically modified polymers and/or synthetic polymers.

17. The biopsy instrument according to claim 1, wherein the biopsy instrument has a longitudinal bore configured to receive a mandrin.

18. The biopsy instrument of claim 1 for endoscopic applications further comprising an adaptor and/or a longitudinally movable sheath.

19. The biopsy instrument according to claim 9, wherein the magnetic element has an outer diameter that is 0.0001 mm to 5 mm smaller than the outer diameter of the distal portion of the guide element.

20. The biopsy instrument according to claim 9, wherein the magnetic element has an outer diameter that is 0.01 mm to 0.1 mm smaller than the outer diameter of the distal portion of the guide element.

21. The biopsy instrument according to claim 1, wherein the stabilizing element is adhesively bonded and/or welded to the proximal portion of the guide element.

22. A method for binding microorganisms, tumor cells, trophoblasts, biomarkers or other cell populations or molecules, the method comprising providing the biopsy instrument according to claim 1, wherein the method comprises:
  i. coupling one or more ligands to magnetic nanoparticles;
  ii. binding said ligands to microorganisms, tumor cells, trophoblasts, biomarkers or other cell populations or molecules;
  iii. binding the magnetic nanoparticles to at least one magnetic element of the biopsy instrument.

23. The method according to claim 22,
wherein the one or more ligand is oligoacyllisin and/or a glycopeptide antibiotic.

24. The method of claim 22 further comprising enriching samples from the vascular system, efferent glandular ducts of the pancreas, lachrymal gland, parodit gland, efferent ducts of the mucosal glands, mixed glands, cutaneous and sebaceous glands, mammary gland, spinal canal, brain chamber system, peridural space, gall bladder and its efferent anatomical structures, efferent urinary tracts or the lymphatic system, body cavities of the abdomen or the chest, the uterus, the urogenital apparatus, or a joint or the gastrointestinal tract.

25. The method of claim 22, wherein said method is a diagnostic method which includes prenatal diagnosis, cancer diagnosis and therapy follow-up as well as diagnosis of a disease selected from the group consisting of inherited diseases, proliferative diseases, inflammatory diseases, autoimmune diseases, infectious diseases, hormonal disorders, diseases of blood and blood-forming organs, diseases of the digestive tract, liver, bile, pancreas, diseases of the urogenital tract and the kidney, diseases of the heart, abnormal changes in the vascular system and lymphatic system, pulmonary diseases, diseases of the central or peripheral nervous system and of the electrical stimulus transmission, and neurodegenerative diseases.

26. The method of claim 25,
wherein the diagnosis of infectious disease refers to a diagnosis of a disease caused by parasitic, bacterial or viral infection, the prenatal diagnosis refers to a diagnosis of gene mutations, chromosome mutations and chromosome aberrations from the group of a deletion, inversion, duplication, translocation and of ring chromosomes, or of a malfunction of gene transcription, gene translation, mRNA stability, of a splice variant, of a malfunction of the mRNA transport into the cytoplasm, of the protein biosynthesis and/or an epigenetic factor; the cancer diagnosis is used as a primary diagnosis, diagnosis for tumor spread, or for tumor grading; the therapy follow-up refers to monitoring a tumor treatment, monitoring an autologous, syngeneic, allogeneic, xenogeneic or alloplastic transplantation, monitoring an inflammatory disease, monitoring an infectious disease, monitoring a hormonal disease, monitoring a psychiatric disorder or monitoring a neurodegenerative disease; the hereditary disease is selected from the group consisting of an autosomal recessive, autosomal dominant, gonosomal and mitochondrial and/or extra-chromosomal hereditary disease, or a disease that can be attributed to a genetic disposition; the proliferative disease is selected from the group consisting of a tumor, precancerosis, dysplasia, neuroendocrine tumor, endometriosis and metaplasia; the autoimmune disease is selected from the group consisting of rheumatoid arthritis, inflammatory bowel disease, osteoarthritis, neuropathic pain, alopecia areata, psoriasis, psoriatric arthritis, acute pancreatitis, allograft rejection, allergies, allergic inflammation of the lung, multiple sclerosis, Alzheimer's disease, Crohn's disease and systemic lupus erythematous; the infectious disease is selected from the group consisting of parasitic diseases, bacterial diseases or viral diseases; or the hormonal disease is selected from the group consisting of diseases of sugar metabolism, lipid metabolism, protein metabolism, sexual development and reproduction, water-salt balance, growth and cell formation.

27. The method of claim 24, wherein the method comprises a minimal invasive surgical procedure.

28. A biopsy instrument for the enrichment of sample material, comprising:
  i. a non-magnetic guide element comprising a spring-elastic most distal portion of the guide element and a proximal portion,
  ii. a magnetic element that is fitted between the distal portion and the proximal portion of the guide element, and
  iii. a non-magnetic stabilizing element connected to the proximal portion of the guide element, wherein the magnetic element is configured to be releasably attached to the guide element and/or wherein the stabilizing element is configured to be reversibly connected to the proximal portion of the guide element, wherein the biopsy instrument is configured for the enrichment of the sample material and for insertion into a body of a subject, and wherein the stabilizing element is configured to stabilize the magnetic element during a biopsy and to avoid dislocation of the magnetic element.

* * * * *